United States Patent [19]

Cerbelaud et al.

[11] Patent Number: 5,034,329
[45] Date of Patent: Jul. 23, 1991

[54] PROCESS FOR THE PREPARATION OF OPTICALLY ACTIVE 2-ARYLALKANOIC ACIDS

[75] Inventors: Edith Cerbelaud; Dominique Petre, both of Lyons, France

[73] Assignee: Rhone-Poulenc Sante, Antony, France

[21] Appl. No.: 302,193

[22] Filed: Jan. 27, 1989

[30] Foreign Application Priority Data

Jan. 27, 1988 [FR] France ................ 88 00924

[51] Int. Cl.$^5$ ............................................. C12P 7/52
[52] U.S. Cl. ..................................... 435/280; 435/141
[58] Field of Search ............................... 435/280, 141

[56] References Cited

U.S. PATENT DOCUMENTS 3,940,316 2/1976 Commeyras et al. .
4,366,250 12/1982 Jallageas et al. .
4,812,403 3/1989 Boesten et al. ...................... 435/141

FOREIGN PATENT DOCUMENTS 0187680 7/1986 European Pat. Off. .
0227078 7/1987 European Pat. Off. .
1342844 10/1963 France .
2447359 8/1980 France .
949669 2/1964 United Kingdom .
8607386 12/1986 World Int. Prop. O. .

OTHER PUBLICATIONS

Chemical Abstracts, vol. 91, 1979, p. 610.
Chemical Abstracts, vol. 83, 1975, pp. 471-472 (27810).
Chemical Abstracts, vol. 81, 1974, p. 376.
Zbl. Bakt. Hyg., I. Abt. Orig. A220, 452-456 (1972) Frommer et al.
Thiery et al., Chem. Abst. vol. 105 (1986), p. 167,595w.
Dotani et al., Chem. Abst. vol. 104 (1986), p. 166,912q.

*Primary Examiner*—Sam Rosen
*Attorney, Agent, or Firm*—Morgan & Finnegan

[57] ABSTRACT

Optically active 2-arylalkanoic acids are made by enantioselective hydrolysis of the corresponding racemic amides in the presence of a microorganism, or of an enzyme derived therefrom, able selectively to hydrolyse racemic α-phenylpropionamide to S α-phenylpropionic acid.

8 Claims, No Drawings

PROCESS FOR THE PREPARATION OF OPTICALLY ACTIVE 2-ARYLALKANOIC ACIDS

The present invention relates to the preparation of optically active 2-arylalkanoic acids of general formula:

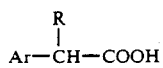

in which Ar denotes an unsubstituted or substituted aromatic radical and R denotes an ethyl, propyl or isopropyl radical, by enantioselective hydrolysis of the corresponding racemic amides.

More particularly, the present invention relates to the preparation of the S (+) enantiomers of the 2-arylalkanoic acids of general formula (I), and especially to the preparation of the S (+) enantiomers of 2-phenyl-3-methylbutyric acids of general formula:

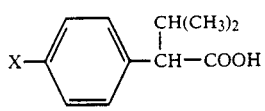

in which X denotes a halogen atom, preferably a chlorine atom, or a methyl radical.

It is known [Y. Kawakami, J. Synth. Org. Chem., 38, 574 (1980)] that esters of general formula:

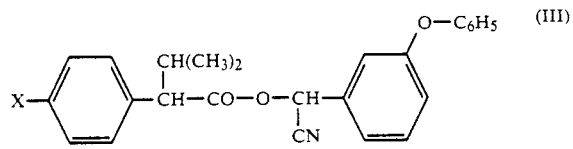

in which X is defined as above, have remarkable insecticidal properties. In general formula (III), the presence of 2 asymmetric carbons results in the possibility of the existence of 4 optical isomers. Among these Isomers, those derived from the S (+) isomers of the acids of general formula (II) have an activity which is superior to that of the corresponding racemic products (see DE 2,737,297).

It is known [H. Nohira et al., Agric. Biol. Chem., 50, 675 (1986)] to prepare the optically active isomers of the products of general formula (II) by preferential crystallization of the diethylamine salt of the acid of general formula (II).

It has now been found, and this forms the subject of the present invention, that the S form 2-arylalkanoic acids of general formula (I) may be obtained by enantioselective hydrolysis of the corresponding racemic amides using a microorganism, or enzyme derived therefrom, chosen for its ability to hydrolyse racemic α-phenylpropionamide to S α-phenylpropionic acid.

The selection of the agent (microorganism or enzyme) which promotes the enantioselective hydrolysis of the racemic amides of 2-arylalkanoic acids of formula (I) is made by bringing the agent into contact with racemic α-phenylpropionamide in a suitable medium until 20% of the amide has been converted, and by then measuring the enantiomeric excess. An agent which, under these conditions, hydrolyses racemic α-phenylpropionamide to S α-phenylpropionic acid with an enantiomeric excess higher than 65% is suitable for use in the present invention.

Particularly suitable microorganisms belong to the genera Brevibacterium and Corynebacterium and, more particularly, to the species Brevibacterium R 312 (CBS 717.73), Corynebacterium N 771 (FERM P 4445), and Corynebacterium N 774 (FERM P 4446), which make it possible to obtain S 2-arylalkanoic acids with an enantiomeric excess of S isomer which is generally higher than 90%.

It is surprising to find that, among these microorganisms, Brevibacterium R 312, which is described in FR 79/01,803/2,447,359 published August 22, 1980, in which it is stated that that microorganism has been deposited with the Centraal Bureau voor Schimmelcultures, Oosterstraat 1, P O Box 273, 3740, AG Baarn, Netherland, as CBS 717 73, and in Advances in Biochemical Engineering, vol. 14, p. 1-32 (1980) as containing a nonstereospecific general amidase, hydrolyses stereospecifically the racemic amides of the 2-arylalkanoic acids of general formula (I), while its $A_4$ mutant which contains an L stereospecific amidase does not hydrolyse the racemic amides of the 2-arylalkanoic acids of general formula (I) stereoselectively.

It should also be noted that Corynebacterium N 771 and Corynebacterium N 774, which are described in EP 0,187, 680 in which it is stated that these microorganisms were deposited with the Fermentation Research Institute, Agency of Science and Technology, 1,3-Higashi 1-chome, Yatabemachi, Tsukuba-gun, Ibaraki-ken, Japan, on May 30, 1978 as FERM P—4445 and FERM P—4446 respectively, hydrolyse, for example, lactonitrile to D,L lactic acid and α-aminophenylpropionitrile to D,L-phenylalanine without stereoselectivity.

The process of the present invention is generally carried out in a homogenous or heterogeneous aqueous or aqueous organic medium, under temperature and pH conditions determined by the nature of the microorganism and of the enzyme, by agitating a suspension of cells, or of a cell extract, of the microorganism and the racemic amide of the 2-arylalkanoic acid.

The process produces a mixture of the S 2-arylalkanoic acid and the R amide of the 2-arylalkanoic acid. The latter may then be racemised by known techniques to a racemic amide of the 2-arylalkanoic acid, which can again be hydrolysed to the S 2-aryl alkanoic acid under the conditions described above. For example, the racemisation may be performed by heating in aqueous ammonia at a temperature of between 80° and 160° C.

When the microorganism employed has the property of hydrolysing nitriles, combined with the property of hydrolysing α-phenylpropionamide enantioselectively, an S 2-arylalkanoic acid can be obtained either from the nitrile of the racemic 2-arylalkanoic acid (which is hydrolysed in situ to the racemic amide) or from the amide of the racemic 2-arylalkanoic acid.

The following Examples illustrate the invention.

EXAMPLE 1 a) The strain Brevibacterium R 312 (CBS 717.73) is cultured in an agitated flask at 28° C. for 14 hours in a medium having the composition:

| | |
|---|---|
| glucose | 10 g |
| $(NH_4)_2SO_4$ | 5 g |
| $KH_2PO_4$ | 1.01 g |
| $Na_2HPO_4.12H_2O$ | 1.64 g |
| $K_2HPO_4$ | 0.82 g |

| -continued | |
|---|---|
| CaCl$_2$.2H$_2$O | 0.012 g |
| ZnCl$_2$ | 0.0012 g |
| FeSO$_4$.7H$_2$O | 0.0012 g |
| MnSO$_4$.H$_2$O | 0.0012 g |
| MgSO$_4$.7H$_2$O | 0.5 g |
| Thiamine hydrochloride | 0.002 g |
| Water q.s. | 1000 cc |

This preculture is employed for seeding a culture medium having the same composition but additionally containing N-methylacetamide at the concentration of 20 mM. The culture is carried out in an agitated flask for 24 hours at 28° C. The biomass obtained is separated by centrifuging and is then washed twice with a sodium chloride solution at a concentration of g/liter.

b) A centrifugation pellet containing Brevibacterium R 312 cells (13 mg, expressed as solids content) is suspended in phosphate buffer (50 mM; 2 cc) at pH=7. Racemic 2-phenylpropionitrile (25 mg, 190 μmol) is added. After 24 hours' agitation at 25° C., the reaction mixture is diluted by adding a mixture of acetonitrile and N hydro-chloric acid (90/10 by volume; 23 cc). The bacteria are removed by centrifuging. The composition of the supernatant is determined by high performance liquid chromatography (HPLC).

The supernatant contains:
2-phenylpropionamide (119 μmol)
2-phenylpropionic acid (62 μmol).

Sodium chloride is added to promote the separation of the aqueous or organic phases. After evaporation of the organic phase to dryness, the residue is taken up with a mixture of chloroform and 0.1N sodium hydroxide (1/1 by volume; 20 cc). The basic phase is acidified and is then extracted with chloroform. Measurement of the rotatory power of the extract 2-phenylpropionic acid shows that the enantiomeric excess of S (+) isomer is 100%.

After forming a derivative of 2-phenylpropionic acid with R (+) α-methylbenzylamine, analysis by HPLC shows that the enantiomeric excess is 96.4%.

EXAMPLE 2

A centrifugation pellet containing Brevibacterium R 312 cells (320 mg, expressed as solids content) is suspended in phosphate buffer (50 mM; 5 cc) at pH=7.0. Racemic 2-(4-chlorophenyl)-3-methylbutyramide (71.2 mg, 337 μmol) is added. After 117 hours agitation at 25° C., the reaction mixture is diluted by addition of a mixture of acetonitrile and N hydrochloric acid (90/10 by volume; 45 cc). The bacteria are removed by centrifuging. The composition of the mixture is determined by high performance liquid chromatography (HPLC).

The supernatant contains:
2-(4-chlorophenyl)-3-methylbutyramide (258 μmol)
2-(4-chlorophenyl)-3-methylbutyric acid (73 μmol).

Sodium chloride is added to promote the separation of the aqueous and organic phases. A mixture of ether and 0.1N sodium hydroxide (3/1 by volume) is added to the organic phase, which is separated by decanting. After the aqueous and organic phases have been separated by decanting and the aqueous phase has been acidified, 2-(4-chlorophenyl)-3-methylbutyric acid is extracted from the aqueous phase with chloroform.

Measurement of the rotatory power shows that the enantiomeric excess of S (+) isomer is 97.5%.

After forming a derivative of the acid with R (+) α-methylbenzylamine, analysis by HPLC shows that the enantiomeric excess is greater than 90%.

EXAMPLE 3

A centrifugation pellet containing Brevibacterium R 312 cells (321 mg, expressed as solids content) is suspended in a phosphate buffer (50 mM; 5 cc) at pH=7.0. Racemic 2-(4-chlorophenyl)-3-methylbutyronitrile (75.9 mg, 392 μmol) is added. After 117 hours' agitation at 25° C., the reaction mixture is diluted by addition of a mixture of acetonitrile and N hydrochloric acid (90/10 by volume; 45 cc). The bacteria are removed by centrifuging. The composition of the mixture is determined by HPLC.

The supernatant contains:
2-(4-chlorophenyl)-3-methylbutyramide (289 μmol)
2-(4-chlorophenyl)-3-methylbutyric acid (78 μmol).

The acid is extracted under the conditions described in Example 2.

After the acid has been converted into a derivative with R (+) α-methylbenzylamine, analysis of the mixture by HPLC shows that the enantiomeric excess of 2-(-4-chlorophenyl)-3-methylbutyric acid is 97% as S (+) isomer.

What is claimed is:

1. A process for the preparation of an S (+) enantiomer of a 2-arylalkanoic acid of the formula:

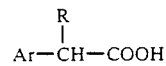

in which Ar denotes an unsubstituted or substituted aromatic radial wherein the substituent is a halogen atom or a lower alkyl group and R denotes ethyl, propyl or isopropyl, which comprises hydrolysing enantioselectively a corresponding racemic amide of a 2-arylalkanoic acid, which may be prepared in situ, in the presence of a microorganism, or of an enzyme derived therefrom, able selectively to hydrolyse racemic α-phenylpropionamide to S α-phenylpropionic acid with an enantiomeric excess higher than 65%, and then separating the S 2-arylalkanoic acid obtained from the amide of R 2-arylalkanoic acid.

2. Process according to claim 1, wherein the microorganism has nitrilase activity as well as the ability enantioselectively to hydrolyse racemic α-phenylpropionamide to S α-phenylpropionic acid.

3. A two-step process according to claim 2, wherein the racemic amide of a 2-arylalkanoic acid is produced in situ by the enzymatic hydrolysis of a racemic 2-arylalkanoic acid nitrile.

4. Process according to claim 1, wherein the microorganism is a Brevibacterium or Corynebacterium.

5. Process according to claim 1, wherein the microorganism is Brevibacterium R 312 (CBS.717.73), Corynebacterium N 771 (FERM P 4445) or Corynebacterium N 774 (FERM P 4446).

6. Process according to claim 2, wherein the microorganisms are chosen from Brevibacterium and Corynebacterium strains.

7. Process according to claim 2, wherein the microorganism is Brevibacterium R 312 (CBS 717.73), Corynebacterium N 771 (FERM P 4445) or Corynebacterium N 774 (FERM P 4446).

8. A two-step process according to claim 1, wherein an acid of formula:

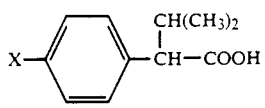
in which X denotes a halogen atom or methyl radical, in S (+) form, is produced from a corresponding racemic amide or nitrile.
* * * * *
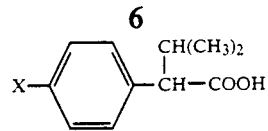
in which X denotes a halogen atom or methyl radical, in S (+) form, is produced from a corresponding racemic amide or nitrile.
* * * * *